United States Patent [19]

Frankel et al.

[11] 4,041,940
[45] Aug. 16, 1977

[54] CONTOURED KNEE IMMOBILIZER

[76] Inventors: S. Arthur Frankel, 2 Poly Drive, Billings, Mont. 59101; Glenn F. Cueman, R.D. 3, Lake Sharon, Warsaw, Ind. 46580

[21] Appl. No.: 629,192

[22] Filed: Nov. 5, 1975

[51] Int. Cl.² ............................................. A61F 3/00
[52] U.S. Cl. ............................ 128/80 C; 128/87 R; 2/24
[58] Field of Search ............ 128/89 R, 87 R, 80 R, 128/80 C, 88, 165; 2/24, 22

[56] References Cited

U.S. PATENT DOCUMENTS

| 158,893 | 1/1875 | Bissell | 128/88 |
|---|---|---|---|
| 1,228,113 | 5/1917 | Hinson | 128/88 |
| 2,625,453 | 1/1953 | Lampe et al. | 128/80 C |
| 3,853,123 | 12/1974 | Moore | 128/80 C |
| 3,888,244 | 6/1975 | Lebold | 128/165 |
| 3,911,497 | 10/1975 | Lewis, Jr. et al. | 2/24 X |

FOREIGN PATENT DOCUMENTS

| 7,337 | 1/1837 | United Kingdom | 128/88 |
|---|---|---|---|

*Primary Examiner*—John D. Yasko
*Attorney, Agent, or Firm*—Richard H. Brink; David J. Mugford

[57] ABSTRACT

A knee immobilizer having a rigid U-shaped shell to fit around the back of the leg extending from well above to well below the knee, the axes of the upper and lower portions being at an angle of 170°. A soft cushion larger and much thicker than the shell lies between the shell and the leg. A rigid front thigh plate and a rigid front shin plate each have soft cushions and are attached to the shell by straps which pass through slots in the shell and plates and are provided with hook and loop fasteners.

4 Claims, 7 Drawing Figures

CONTOURED KNEE IMMOBILIZER

This invention relates to a body appliance and, particularly, to an orthopedic appliance for immobilizing a leg.

Orthopedic appliances of this general character have been developed in the past for the primary purpose of holding the leg of a patient in a rigid posture, particularly during the recovery interval following surgery on the leg and particularly on the knee joint. For many years, plaster casts and the like were used to immobilize a leg following surgery so that the joint and surrounding tissues could heal in a manner most advantageous and comfortable to the patient. Because of the fact that plaster casts are heavy and cumbersome and require considerable professional time in application, removal and reapplication in subsequent examinations of the surgically treated region, there has been a continuing effort to develop specialized braces which are more easily applied and removed and which are considerably more comfortable for the patient to wear over an extended period of time.

It is an object of the present invention to provide a substantially improved orthopedic appliance of this general nature in which the appliance is more easily applied and removed and in which the comfort is greater and, further, in which the leg is maintained at a proper flexion angle to maximize recovery.

Briefly described, the invention includes an elongated substantially rigid shell in the form of a channel have a substantially U-shaped cross-section, the shell including an upper tapered portion to be fitted about the leg above the knee, a lower tapered portion to be fitted about the leg below the knee and a midportion rigidly connecting the upper and lower portions with the axes of the upper and lower portions oriented at an obtuse angle. Cushioning means is carried within the shell to be disposed between the leg and the shell for cushioning the leg received in the shell. Securing means is provided for releasably securing the shell to the leg. The angle between the axes of the upper and lower portions is preferably about 170°.

In order that the manner in which the foregoing and other objects are attained in accordance with the invention can be understood in detail, a particularly advantageous embodiment thereof will be described with reference to the accompanying drawings, which form a part of this specification, and wherein.

Figure 1:
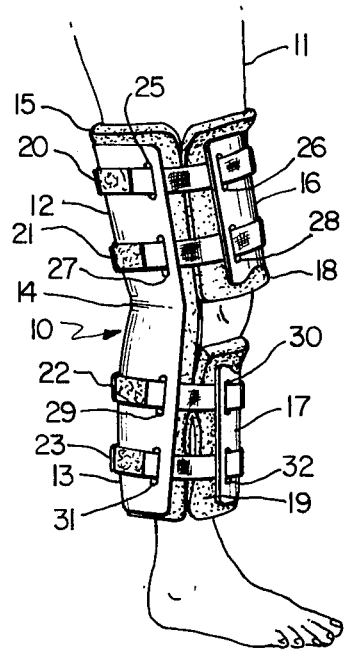
FIG. 1 is a side elevation of a device according to the invention, shown applied to the leg of a patient.
Figure 2:
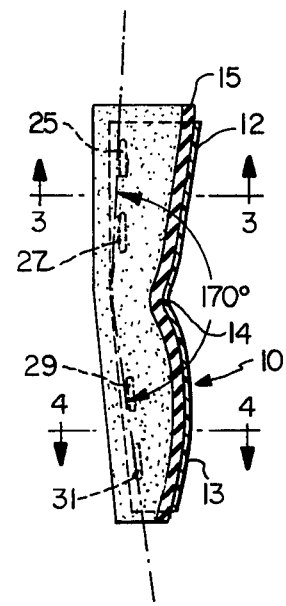
FIG. 2 is a side elevation, in section, of the major shell portion of the device of FIG. 1.
Figure 3:
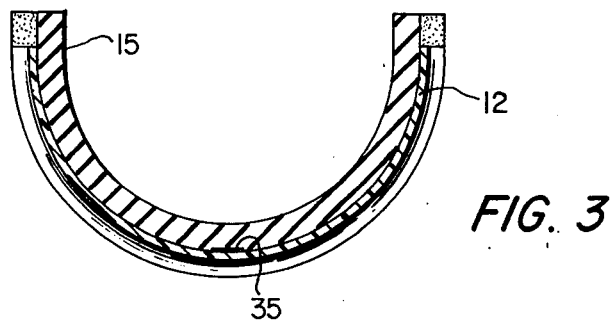
Figure 4:
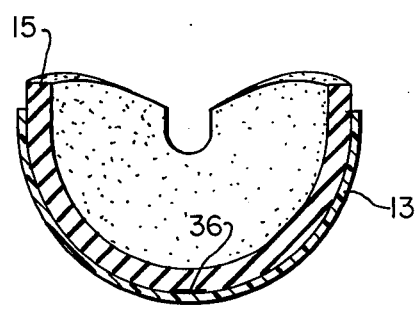
Figure 5:
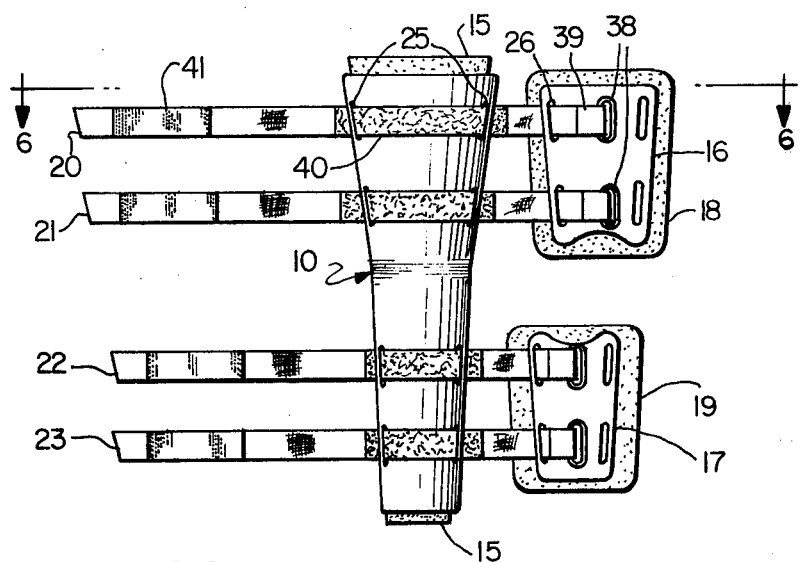
Figure 6:
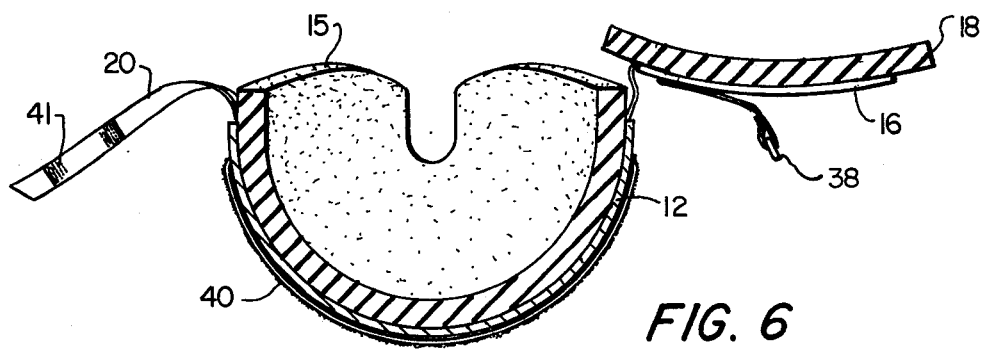

FIGS. 3 and 4 are sectional views along lines 3—3 and 4—4, respectively, of FIG. 2;

FIG. 5 is a rear elevation of the apparatus of FIG. 1 in an open condition before application to a patient's leg;

FIG. 6 is a section along lines 4—4 of FIG. 3; and

Figure 7:
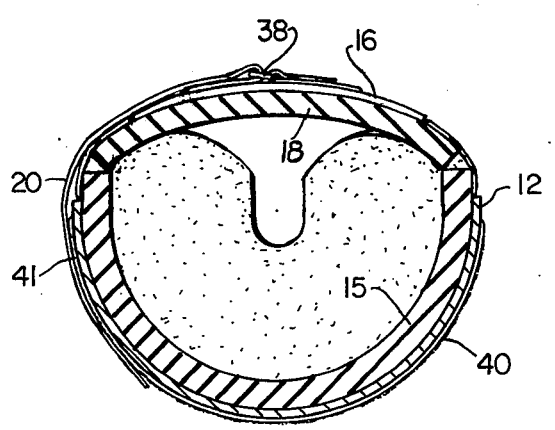

FIG. 7 is a sectional view similar to FIG. 4 but showing the device in its closed position as applied to a leg.

As shown in FIG. 1 the device according to the present invention includes an elongated substantially rigid shell indicated generally at 10 which is shaped to fit around the back portion of the leg 11 extending above and below the knee of the patient, the shell including an upper tapered portion 12 which fits about the back of the leg above the knee, a lower tapered portion 13 which fits about the leg below the knee, and a midportion 14 which fits about the leg at the region of the knee, the midportion rigidly connecting the upper and lower portions so that the axes of the upper and lower portions are oriented at an obtuse angle which is, preferably, about 170°. Cushioning means, comprising a continuous relatively thick pad 15 of soft spongy material is carried within the shell and disposed between the shell and the leg for cushioning the leg received by the shell. In order to firmly attach the shell to the leg there is provided securing means including an upper front plate 16 and a lower front plate 17, plates 16 and 17 being designed to fit against the thigh and shin portions of the leg, respectively. Cushioning pads 18 and 19 are held by plates 16 and 17 and lie between the plates and the leg. Plate 16 is held in position by straps 20 and 21 and plate 17 is held in place with respect to the shell by straps 22 and 23. Strap 20 passes through slots 25 in upper portions 12 of shell 10 and through slots 26 in plates 16. In similar fashion, strap 21 passes through slots 27 in shell 10 and 28 in plate 16, while strap 22 passes through slots 29 in lower portion 13 of shell 10 and slots 30 in plate 17, and strap 23 passes through slots 31 in portion 13 and slots 32 in plate 17.

As best seen in FIGS. 2-4, shell 10 is in the nature of a channel having a generally U-shaped cross-section with the upper portion being nearly semi-circular, tapering from its upper end to midportion 14 which is smaller in diameter than the adjacent portion of upper portion 12. Lower portion 13 enlarges from its junction with the midportion and then tapers to a smaller, lower end, conforming generally to the usual shape of the calf portion of the patient's leg. These portions of the shell are, of course, not clearly or precisely distinguishable by any definite line of demarcation, but the regions thereof can be seen to conform generally to the portion of the leg which they fit.

Because of individual variations between legs of patients with which the device is to be used, it will be recognized that the shaping of the shell only generally conforms to the shape of the leg. Individual variations are accommodated by the rather thick foam pad 15 which is polyurethane foam and is in the order of ¾ inches (19 mm) thick. Shell 10 is formed from high density white polyethylene and has a thickness of approximately ⅛ inches (3 mm), so that the ratio of the thickness of the pad to the thickness of the shell is in the order of 6:1. As will be seen in FIG. 2, portion 14 joins portions 12 and 13 so that the central axes of the upper and lower portions intersect to form an angle of approximately 170° or, stated differently, so that the central axes of these portions are out of alignment of about 10°, resulting in 10° of flexion of the leg when it is immobilized by the device of the present invention. It is found that this angle is a particularly comfortable and advantageous angle in which to restrain and immobilize a leg during recovery after patellar or related surgery.

As seen in FIGS. 3 and 4, a strip of pressure-sensitive adhesive material 35 is provided on the inner surface of shell portion 12 and a similar strip 36 of pressure-sensitive adhesive material on the inner surface of portion 13. These adhesive strips are adhesive on both sides so that pad 15 is retained within the channel of shell 10 in proper position and need not be separately positioned or handled when applying the device to the patient's leg. However, the adhesive permits the foam cushion to be removed for cleaning or for replacement, if necessary.

The assembly is shown in FIG. 5 in a spread-out form as it might be before application to a patient's leg. As seen therein, each of straps 20-23 is provided at one end with a simple rectangular buckle 38 which is retained at the strap end by a looped-over portion and conventional stitching 39. Using strap 20 as an example, the strap is normally assembled so that is passes through one of slots 26 in plate 16 with its associated buckle 38 adjacent the outer surface of plate 16. The strap is then passed through slots 25 in shell portion 12 so that the major portion of the strap lies outside of the shell. This portion of the strap is provided with a length of looped fabric 40 on its outer surface, the distal end of the strap being provided with a length of material 41 having a plurality of small hooks which are capable of engaging the looped fabric. Portion 41 is provided on the same side of strap 20 as material 40, this combination of hooks and loops constituting a fabric of the type conventionally available under the trademark VELCRO.

Each of these straps is provided with this loop and hook arrangement. The strap is then ready, as shown in FIG. 6, to be placed around the leg, the leg being omitted from FIGS. 5-7 for simplicity.

Also as seen in FIG. 5, each of plates 16 and 17 is in the shape of an isosceles trapezoid with an inwardly curved end, upper plate 16 having the curved end facing downwardly and plate 17 having the curved end face upwardly, i.e., toward the knee. Foam pads 18 and 19 are generally rectangular in shape and are larger than their respective plates to avoid contact of the plate edges with the patient's leg.

When applying the device, the upper front securing means including plate 16 and pad 18 is placed across the front of the leg as shown in FIG. 7 and the end of strap 20 having hooked material 41 is passed through the other one of slots 26 and then through the buckle 38 at the opposite end of the same strap. The strap is then brought back around the same side of the shell and tightened to the desired degree, whereupon the hooks are caused to engage the loop or pile portion of the fabric 40 in the location which will retain the structure firmly against the leg. Each of the other straps is then engaged in a similar path, locking the structure on the leg in the manner shown in FIG. 1. Additional straps, not shown, may be employed around the entire assembly if desired or may be used in the vicinity of the patella if this is deemed desirable by the attending physician. When the straps are tightened, whether or not additional straps are used, the foam padding is compressed within the rigid shell between the shell and plate portions and the leg, allowing substantial support but minimizing the "tourniquet" effect and avoiding any localized pressure points. Migration of the structure as a result of the thick pad compression in the rigid shell is minimized. The fact that the shell is preformed as a rigid structure decreases the force which must be employed in applying the device to the patient's leg and contributes to comfortable and effective distribution of the forces which maintain it in its proper position and which maintain the leg immobilized in the flexion angle previously described.

While one advantageous embodiment has been chosen to illustrate the invention, it will be understood by these skilled in the art that various changes are modifications can be made therein without departing from the scope of the invention as defined in the appended claims.

What is claimed is:

1. A contoured knee immobilizing device comprising
    a unitary elongated substantially rigid shell in the form of a channel having a substantially U-shaped cross-section, said shell including
        an upper tapered portion to be fitted about the leg above the knee,
        a lower tapered portion to be fitted about the leg below the knee, and
        a midportion having a semi-circular dimension less than the adjacent portions of said upper and lower portions rigidly connecting said upper and lower portions with the axes of said upper and lower portions oriented at an obtuse angle of about 170°;
    cushioning means carried within said shell to be disposed between the leg and said shell for cushioning the leg received by said shell;
    a substantially rigid upper plate in the form of an inverted isosceles trapezoid with a curved recess at the bottom edge thereof adjacent said upper portion;
    a substantially rigid lower plate in the form of an inverted isosceles trapezoid with a curved recess at the top edge thereof adjacent said lower portion;
    foam pads coupled to said upper plate and said lower plate; and
    straps coupled to said shell including a looped fabric located on one face of each strap and looped-fabric engaging hooks located on the same face of each strap for releasably coupling straps onto said upper and lower plates;
    wherein said cushioning means and said foam pads are adapted to wholly encompass the human leg except for the patella.

2. A device according to claim 1 wherein said cushioning means includes a continuous foam pad and said device further includes means for coupling said pad to the inner surface of said shell, said pad covering the entire inner surface thereof.

3. A device according to claim 2 wherein the ratio of the thickness of said foam pad to the thickness of said shell is about 6:1.

4. A device according to claim 1 wherein said shell is formed of rigid polymeric material.

* * * * *

UNITED STATES PATENT OFFICE
CERTIFICATE OF CORRECTION

PATENT NO. : 4,041,940
DATED : August 16, 1977
INVENTOR(S) : S. ARTHUR FRANKEL ET AL It is certified that error appears in the above-identified patent and that said Letters Patent are hereby corrected as shown below:

At Column 2, line 60, after the word "material" and before the word "on" insert -- is provided --.
At Column 3, line 16, after the word "fabric" and before the word "of" insert -- fastener --.
At Column 4, line 6, "these" should read -- those --.
At Column 4, line 41, after the word "coupling" and before the word "straps" insert -- said --.

Signed and Sealed this

Twentieth Day of December 1977

[SEAL]

Attest:

RUTH C. MASON
*Attesting Officer*

LUTRELLE F. PARKER
*Acting Commissioner of Patents and Trademarks*